(12) United States Patent
Beddow

(10) Patent No.: US 9,983,316 B2
(45) Date of Patent: May 29, 2018

(54) RADIOACTIVE MATERIAL ASSAYING

(71) Applicant: SOLETANCHE FREYSSINET S.A.S., Rueil-Malmaison (FR)

(72) Inventor: Helen Beddow, Newbury (GB)

(73) Assignee: SOLETANCHE FREYSSINET S.A.S., Rueil-Malmaison (FR)

(*) Notice: Subject to any disclaimer, the term of this patent is extended or adjusted under 35 U.S.C. 154(b) by 0 days. days.

(21) Appl. No.: 15/314,276

(22) PCT Filed: May 28, 2015

(86) PCT No.: PCT/EP2015/061780
§ 371 (c)(1),
(2) Date: Nov. 28, 2016

(87) PCT Pub. No.: WO2015/181268
PCT Pub. Date: Dec. 3, 2015

(65) Prior Publication Data
US 2017/0199282 A1 Jul. 13, 2017

(30) Foreign Application Priority Data
May 28, 2014 (GB) .................................. 1409467.6

(51) Int. Cl.
*G01T 1/167* (2006.01)
*G01N 33/24* (2006.01)
*G21F 9/34* (2006.01)

(52) U.S. Cl.
CPC ............. *G01T 1/167* (2013.01); *G01N 33/24* (2013.01); *G21F 9/34* (2013.01)

(58) Field of Classification Search
CPC ............ G01N 33/24; G01T 1/167; G21F 9/34
See application file for complete search history.

(56) References Cited

U.S. PATENT DOCUMENTS 4,617,169 A 10/1986 Brodzinski et al.
4,742,226 A 5/1988 De Filippis
(Continued)

FOREIGN PATENT DOCUMENTS

CN 103308936 A 1/2010
EP 3208250 A2 1/1987
(Continued)

OTHER PUBLICATIONS

Agarwal, Chhavi, "Summary and Conclusions," Nondestructive Assay of Nuclear Materials by Gamma Ray Spectrometry, Chapter 7, Thesis, Homi Bhabha National Institute, Mar. 2011, pp. 196-203.
(Continued)

*Primary Examiner* — Mark R Gaworecki
(74) *Attorney, Agent, or Firm* — Withrow & Terranova, P.L.L.C.; Vincent K. Gustafson

(57) ABSTRACT

A method of assaying potentially radioactive material comprises selecting a plurality of samples from a material mass on a site (200). In a sequence of steps (104, 106, 108, 110, 112), an activity measurement based on a gross count of each of the samples (212) in the plurality of samples is performed on the site (200), and the activity measurement is compared with one or more activity thresholds in order to categorize the radioactive material for disposal purposes. The threshold(s) and/or activity measurement are based on an assumed parameter set. In a further step (114), sample x from every y of the plurality of samples is selected, where x<y, and a spectroscopic measurement of the emitted radiation from the sample x is performed on the same site (200). In a further step (116), it is automatically determined whether the spectroscopic measurement corroborates the assumed parameter set before the y samples leave the site (200) for disposal purposes.

20 Claims, 2 Drawing Sheets

(56) References Cited

U.S. PATENT DOCUMENTS

Figure 1:
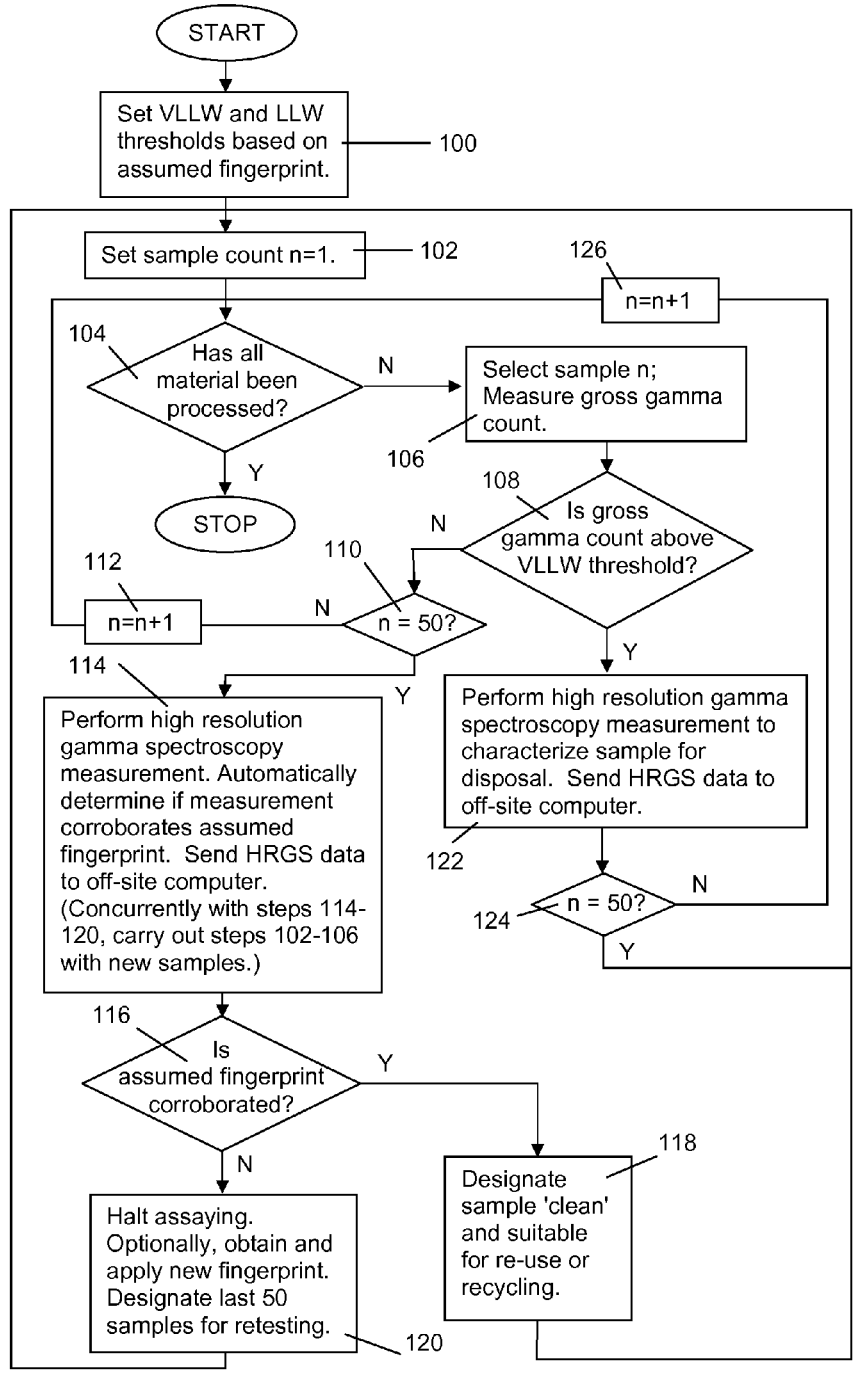

| | | |
|---|---|---|
| 6,448,564 B1 | 9/2002 | Johnson et al. |
| 2007/0108379 A1 | 5/2007 | Rowland et al. |
| 2010/0137148 A1 | 6/2010 | Kaye |
| 2011/0205361 A1 | 8/2011 | Guillot et al. |
| 2011/0258151 A1 | 10/2011 | Gentile et al. |
| 2011/0295537 A1 | 12/2011 | Akers et al. |
| 2012/0311933 A1 | 12/2012 | Reinhard et al. |

FOREIGN PATENT DOCUMENTS

| | | |
|---|---|---|
| JP | S6370186 A | 3/1988 |
| JP | S63173987 A | 7/1988 |
| JP | 2003-075540 A | 3/2003 |
| JP | 2010-203863 A | 9/2010 |
| WO | 2011/131339 A2 | 10/2011 |
| WO | 2013/006898 A1 | 1/2013 |

OTHER PUBLICATIONS

Beddow, H. et al., "Application of Bulk Assay Technologies," Annual Meeting of the International Network of Laboratories for Nuclear Waste Characterization (LABONET), Dec. 10-12, 2013, Vienna, Austria, 7 pages.

Hurtado, S. et al., "An intercomparison of Monte Carlo codes used for in-situ gamma-ray spectrometry," Radiation Measurements, vol. 45, No. 8, Sep. 2010, pp. 923-927.

Oshima, M. et al., "Multiple gamma-ray detection method and its application to nuclear chemistry," Journal of Radioanalytical and Nuclear Chemistry, vol. 278, No. 2, Nov. 2008, pp. 257-262.

Ridikas, D. et al., "Non-Destructive Method of Characterisation of Radioactive Waste Containers Using Gamma Spectroscopy and Monte Carlo Techniques," Radiation Protection Dosimetry, vol. 115, Nos. 1-4, 2005, pp. 113-116.

Salako, Qansy et al., "Analysis of Long-Lived Radionuclidic Impurities in Short-Lived Radiopharmaceutical Waste Using Gamma Spectrometry," Health Physics, vol. 72, No. 1, Jan. 1997, pp. 56-59.

Savidou, A. et al., "Characterization of Radioactive Waste Drums by Non Destructive Gamma Spectrometry," 4th International Conference on NDT, Oct. 11-14, 2007, Chania, Crete-Greece, Hellenic Society for NDT, 5 pages.

Tzika, Faidra et al., "Nondestructive Characterization of Radioactive Waste Drums by Gamma Spectrometry: A Monte Carlo Technique for Efficiency Calibration," Health Physics, vol. 93, Suppl. 3, No. 5, Nov. 2007, pp. 174-179.

Yalcin, S. et al., "The radioactivity measurements in soil, coal and water in south Marmara region of Turkey," Radiation Measurements, vol. 42, 2007, pp. 281-285.

Search Report for United Kingdom Patent Application No. GB1409467.6 dated Nov. 27, 2014, 3 pages.

Notification of Transmittal of International Search Report and the Written Opinion (Form PCT/ISA/220), International Search Report (Form PCT/ISA/210), and Written Opinion (Form PCT/ISA/237) of the International Searching Authority for International Patent Application No. PCT/EP2015/061780 dated Sep. 18, 2015, 10 pages.

RADIOACTIVE MATERIAL ASSAYING

This application is a 35 U.S.C. § 371 national phase filing of International Application No. PCT/EP2015/061780 filed on May 28, 2015, and further claims priority to United Kingdom Patent Application No. 1409467.6 filed on May 28, 2014, with the disclosures of the foregoing applications hereby being incorporated by reference herein in their respective entireties.

This application relates generally to material assaying and specifically to efficient and reliable methods of assaying potentially radioactive material.

The advent of nuclear-based technologies, and particularly nuclear energy generation, has created new challenges in waste management. In the face of depleting supplies of fossil fuels and environmental concerns over carbon emissions, the use of nuclear energy sources may be expected to increase to attempt to meet the energy demands of an increasing population. Efficient and reliable radioactive waste management is therefore of great importance.

A significant part of radioactive waste management is assaying or monitoring, i.e. assessing the radioactivity of material in order that it may be dealt with appropriately. For example, for remediation of contaminated areas at a reactor site, characterisation of soil samples is needed to segregate the land into clean and contaminated areas. As another example, radioactive waste for disposal following site decommissioning requires assaying to ensure it is disposed of appropriately according to its level of radioactivity. While the majority of material on a nuclear site may not be contaminated during use, monitoring is used to confirm when material is within the out of scope limits and even 'clean' material may be monitored for reassurance purposes.

The production of potentially radioactive material is not limited to energy generation. For example, the use of nuclear-based medical techniques results in some radioactive material being produced by hospitals. Nevertheless, owing to the relatively large quantity of waste that comes from nuclear energy generation, radioactive material assaying finds applications predominantly in dealing with material from nuclear energy sites and decommissioning such sites.

Contaminated materials vary widely in terms of their levels of radioactivity, the type of emissions (e.g. $\alpha$, $\beta$, $\gamma$) and their half-life, as a result of the different radionuclides they contain. Radioactive material is classified according to its hazard level, and waste is disposed of according to its classification. Nuclear waste having very high levels of radioactivity can be extremely harmful, and special measures are required to dispose of this waste appropriately. Such high level waste (HLW) makes up a very small percentage of radioactive waste, and so it is not practicable to dispose of all radioactive waste as if it were HLW.

Different methods of disposal or recycling are used for waste having different levels of radioactivity, even for waste having relatively low radioactivity. For example, very low level waste (VLLW) may be disposed of in shallow burial sites, while low level waste (LLW) cannot be disposed of this way. It is therefore important to be able to distinguish between different categories of radioactive waste, including relatively low levels. Often excavated material can be classed as 'clean' and can be re-used; however, this may still involve monitoring to assure that there is no contamination present. When contamination is discovered, the radionuclide-specific activities need to be quantified to enable disposal of the material to a controlled landfill waste management operator.

While it is desirable to dispose of lower level waste by more convenient and less expensive means, e.g. burial, it is important to ensure that more hazardous radioactive material is not inadvertently disposed of with lower level waste. This could occur if, for example, an assaying technique were insufficiently accurate to properly assess the radioactivity level. It could also occur if insufficient samples were to be taken of a mass of waste material, such that the samples were not representative of the waste mass as a whole.

As such, it is necessary for assaying techniques to be of high accuracy to ensure that any given waste sample is correctly characterised. However, high accuracy measurements can take a long time to complete, and may require samples to be taken off site for analysis. This limits the number of samples that can be analysed in any given time period, but testing fewer samples increases the risk that the characterisation of the samples is not an accurate representation of the material from which the samples were taken. High accuracy measurements can also be very costly. Additional cost is itself undesirable, and it may also limit the number of samples that can be tested, increasing the chances of waste being incorrectly categorised.

Real-time assaying methods such as gross gamma measurements are known for performing quick analysis of samples (e.g. within 10 seconds). This allows a greater number of samples to be measured in a given time period. For example, the Gamma Excavation Monitor (GEM) offered by Nuvia Limited can measure at least 300 tonnes of material in a day. These methods can be accurate if the type of radioactive material e.g. its radionuclide fingerprint is known in advance and the material being assayed is substantially homogeneous. For instance, a gross gamma system is typically calibrated using a mathematical modelling code in advance. However, these methods can in some cases be unreliable if the measurements are based on inappropriate or incorrect assumptions about the radioactive material (including soil type and density), detector assembly, counting geometry, background etc. For example, if some samples contain radionuclides that deviate from an assumed fingerprint, an incorrect assessment of the radioactivity level may be obtained from an activity measurement based on a gross count. This may lead to an incorrect classification and inappropriate disposal of the waste material. According to UK nuclear industry codes of practice, disposal refers to emplacement of waste in an appropriate facility without the intention of retrieval. It is therefore paramount that waste is categorised correctly for disposal.

Land remediation projects are costly initiatives; therefore it is crucial that monitoring equipment does not have the adverse effect of excessively slowing down the programme of works. There remains a need for rapid screening of materials at the same time as full quantification of radionuclide-specific activities.

The present invention therefore seeks to provide improved methods of radioactive waste assaying.

According to the present invention there is provided a method of assaying potentially radioactive material comprising:

selecting a plurality of samples from a material mass on a site;

performing, on the site, an activity measurement based on a gross count of each of the samples in the plurality of samples, and comparing the activity measurement with one or more activity thresholds in order to categorise the radioactive material for disposal purposes, wherein the threshold(s) and/or activity measurement are based on an assumed parameter set;

selecting a sample x from every y of the plurality of samples, where x<y;

performing, on the same site, a spectroscopic measurement of the emitted radiation from the sample x; and automatically determining whether the spectroscopic measurement corroborates the assumed parameter set before the y samples leave the site for disposal purposes.

The method allows a fast activity measurement based on a gross count so as to achieve a high throughput of test samples in a material assaying process. There may be concerns that such a fast measurement could be unreliable when used on its own, for example when assaying large volumes of potentially radioactive material that may not be homogeneous. However, the provision of a spectroscopic measurement alongside an activity measurement, on the same site, to corroborate the assumed parameter set in relation to x in every y samples improves the accuracy of the overall technique for material assaying. For example, the activity thresholds and/or the activity measurement may be appropriate for categorising the waste correctly if the assumed parameter set fits all of the samples, but inappropriate otherwise. The regular use of additional, spectroscopic data from the spectroscopic measurement to corroborate the parameter set at least for a representative x in every y samples then allows the results of the comparison of the activity measurement with the threshold(s) to be relied upon with greater certainty. The method of the present invention therefore incorporates the advantages of systems having a high throughput of samples while improving the accuracy and reliability of the assaying process.

An advantage of the spectroscopic measurement corroborating the assumed parameter set, on the same site, is that one or more of the y samples can be prevented from leaving the site if it is determined from a sample x that the assumed parameter set was not correct or appropriate for at least some of the material mass. In particular, the method of the present invention comprises comparing the activity of each sample to one or more thresholds. The result of such a comparison is used to characterise each sample for disposal purposes, for example categorising the sample as one of: very low level waste (VLLW) or low level waste (LLW). Each category may have different disposal requirements. Some categories may be safe to leave the site immediately e.g. for re-use. Others may need to be retained on site to be given to disposal specialists for proper disposal or recycling. Any reference herein to disposal purposes will be understood to include recycling of a material as appropriate. Accordingly, in some embodiments, categorising comprises determining whether each sample is safe to leave the site. The method may further comprise: preventing the y samples from leaving the site (e.g. at least until they have been re-tested) when the spectroscopic measurement of a sample x does not corroborate the assumed parameter set.

In addition, or alternatively, the method may optionally further comprise: obtaining a new parameter set when the spectroscopic measurement for a sample x does not corroborate the assumed parameter set. The method may further comprise: continuing the activity measurement for the plurality of samples using one or more new thresholds based on the new parameter set.

A further advantage of performing the spectroscopic measurement on the same site as the activity measurement based on a gross count is that it may allow steps to be taken immediately to control movement of the y samples if the assumed parameter set is found not to be appropriate for some or all of the material mass. In preferred embodiments, therefore, the step of automatically determining whether the spectroscopic measurement corroborates the assumed parameter set is carried out immediately after performing the spectroscopic measurement. This may help to reduce delays further; if the corroboration is checked more quickly, it is possible to take action more quickly in the event that the assumed parameter set is not corroborated. For example, an operator may be notified immediately if the assumed parameter set is not corroborated, and this may immediately trigger an instruction to cease assaying on the site and/or prevent material from leaving the site. Before assaying is recommended, a testing laboratory may be instructed to perform further tests to obtain a new parameter set. Accordingly, a new parameter set may be obtained and operations restarted as quickly as possible. This provides a significant advantage, as radioactive assaying procedures can be very time-sensitive. During projects such as land remediation projects, it is necessary to test a large amount of material. This is to ensure that no material is incorrectly characterised and disposed of inappropriately. The material therefore needs to be processed as fast as possible to avoid unacceptably long project timescales. Any delays, such as waiting for a sample to be taken off site for a high resolution analysis, and waiting for the analysis result to be sent back to the site, slow down the assaying process significantly.

Time may also be wasted if it takes a long time to determine that a parameter set that is in use is inappropriate, as those samples categorised using the inappropriate parameter set may need to be re-tested. In contrast, the present method can identify an inappropriate parameter set very quickly, and so the number of samples that would need to be re-tested may be much smaller. This allows the rapid throughput of the activity measurement to be continued in parallel with the occasional spectroscopic measurements without risking the need to duplicate a significant amount of testing. Preferably the activity measurement and the spectroscopic measurement are performed concurrently. However, it is possible that the activity measurements could be halted during the spectroscopic measurement.

To corroborate, as used herein, has the meaning of "supporting", or "being consistent with", within certain test or comparison criteria. The test or comparison criteria, for example, may specify certain portions of spectroscopic data that should be tested for consistency with corresponding portions of the assumed parameter set. It follows that for spectroscopic data to be deemed to corroborate an assumed parameter set, a full analysis and comparison may not be performed. In particular, the extent of the test performed to establish corroboration may correspond to the extent of an analysis that can be carried out automatically on the spectroscopic data. A full analysis or verification of the assumed parameter set may require an analysis to be carried out by a person.

In a preferred set of embodiments the assumed parameter set comprises one or more radionuclide fingerprints. A radionuclide fingerprint is a representation of the anticipated radionuclide mix of a material, and is often used to characterise radioactive material. For example, a comprehensive list of the radionuclides that are likely to be present in the material, and their relative contributions to the total activity, is commonly known as a fingerprint. A radionuclide fingerprint may comprise radionuclide ratios for a material, which may be used to infer the radioactivity of a sample from the gross count or count rate, for example, using a linear correlation between the measured count rate and the activity (Bq) or specific activity (Bq/g) of the material. The application of a radionuclide fingerprint can simplify the categorisation of material based on overall activity assessments. The fingerprint may include both gamma and non-gamma emitters. Of course the accuracy of such a correlation or categorisation depends on appropriate radionuclide fingerprint(s) being applied in the first place.

In many cases, checking the spectroscopic data for consistency within certain portions of data may be sufficient to identify an inappropriate parameter set (which would not be evident from the activity measurement alone). For example, where the assumed parameter set comprises a fingerprint then this may be corroborated by checking the spectroscopic data relating to one or more radionuclides in the fingerprint, e.g. the presence of peaks indicating the presence of those radionuclides. Checking for corroboration, rather than performing a full spectroscopic assessment of the fingerprint, enables the check to be carried out automatically, with results returned immediately, i.e. the check does not require the uninterrupted attention of a human operator.

Preferably the spectroscopic measurement involves a radionuclide quantification or assessment, such as a high resolution gamma spectroscopy (HRGS) analysis. The spectroscopic measurement preferably assesses a radionuclide fingerprint of each selected sample x. Although alpha spectrometry is possible, gamma spectrometry is more commonly used and can measure a wide range of gamma-emitting radionuclides, including e.g. Eu-152, Mn-54, Eu-154, Eu-155, Co-60, Ba-133, Cs-134, Cs-137, Na-22, Am-241, and natural uranium and thorium decay chains.

As discussed above, automatically determining whether the spectroscopic measurement corroborates the assumed parameter set may comprise comparing portions of data from the spectroscopic measurement and the assumed parameter set. In embodiments where the assumed parameter set comprises a radionuclide fingerprint, the method may comprise determining whether one or more expected radionuclide peaks associated with the assumed fingerprint are present in the spectroscopic measurement, wherein the assumed fingerprint is corroborated if the one or more expected peaks are all present in the spectroscopic measurement.

An advantage of the automatic determining step is that a machine does not get bored or lose concentration. Nevertheless, it may be advantageous to occasionally have a full (or more complete) analysis of the spectroscopic measurement carried out by a human. In some cases, spectroscopic data may be consistent with (and thus corroborate) an assumed parameter set within the test criteria of the automatic determining step, but the assumed parameter set may nevertheless be found inappropriate. For example, it may be automatically determined that the radionuclide peaks expected for an assumed fingerprint are all present, but this would not identify the presence of additional, unexpected peaks that indicate a deficiency in the fingerprinting.

Accordingly, the method may further comprise: a non-automatic step carried out by a human to determine whether the spectroscopic measurement for the sample x verifies the assumed parameter set. The non-automatic step may be carried out off-site, e.g. so that a trained assessor is not required on-site. In cases where such a non-automatic step is used, and otherwise, spectroscopic data obtained in the spectroscopic measurement may be transmitted off-site for review, e.g. in real-time, and preferably the same day. The transmitted data may be used for the non-automatic step by a remote human assessor.

To verify, as used herein, has the meaning of determining within a reasonable level of certainty that the assumed parameter set is appropriate or correct. For example, a full analysis of the spectroscopic data may be carried out to determine whether it is entirely consistent with the assumed parameter set. It will be understood that the verification may be subject to normal measurement uncertainties in the spectroscopic data and the assumed parameter set, which itself may have been derived from test data. It will also be appreciated that while verification may ideally involve determining the suitability of the parameter set with the greatest level of certainty obtainable, in practice, the verification may be subject to constraints such as available time and resources. Preferably, verifying the assumed parameter set provides a greater level of certainty that the parameter set is appropriate or correct than the step of determining whether the assumed parameter set is corroborated by the spectroscopic data.

In embodiments where the assumed parameter set comprises a radionuclide fingerprint, the non-automatic step may comprise: determining whether any peaks are present in the spectroscopic measurement that indicate the presence of one or more radionuclides not included in the assumed radionuclide fingerprint, wherein the assumed fingerprint is verified if no peaks are present in the spectroscopic measurement that are not related to the radionuclides included in the assumed fingerprint.

In embodiments comprising a non-automatic step, preferably the method comprises preventing the y samples from leaving the site when the non-automatic step for the sample x does not verify the assumed parameter set. This ensures that any samples incorrectly characterised, and which may therefore not be safe to leave the site, are kept on site where they can be correctly categorised once a new parameter set has been determined. Accordingly, the method may further comprise: obtaining a new parameter set when the non-automatic step for the sample x does not verify the assumed parameter set. However, it will be appreciated that this further step may be carried out separately from the rest of the method. For example, re-fingerprinting may require suitable sampling followed by spectroscopic measurements and/or radiochemical assessments.

It is common in land remediation projects for removal of samples from the site to occur daily, e.g. at the end of the day. Therefore, the non-automatic step is preferably carried out at least once per day. For example, the non-automatic step may be carried out each day shortly before the categorised samples are allowed to leave the site. The non-automatic step may even be carried out before the categorised samples are moved within the site, as this could otherwise risk other material or site workers being contaminated.

As discussed above, there are numerous situations in which potentially radioactive material needs to be assayed. However, the method of the present invention is particularly advantageous where large amounts of material need to be assayed. This situation commonly arises in dealing with land remediation or site decommissioning. Therefore, in preferred embodiments, the potentially radioactive material is soil.

The activity measurement may be based on any suitable gross count, e.g. comprising alpha, beta and/or gamma emitters. However, in preferred embodiments the activity measurement is based on a gross gamma count. The activity measurement may therefore be carried out by a suitably calibrated gross gamma detector, such as a CsI detector. The detector may be calibrated using a mathematical modelling code.

It may be difficult and wasteful to calibrate a gross radioactivity counter using a mass of material deliberately contaminated with the relevant radionuclides. The method therefore preferably comprises using a Monte Carlo simulation to determine a relationship between gross count and specific activity e.g. based on an assumed fingerprint. For example, the activity measurement may be based on a Monte Carlo N-Particle Transport Code (MCNP). It will be appreciated that the activity measurement may measure one or more of: activity concentration, specific activity or total activity.

The activity measurement is preferably faster than the spectroscopic measurement, e.g. taking less than 30 seconds, preferably around 10 seconds or less, for each sample. The spectroscopic measurement, by way of comparison, may take around 5-15 minutes.

The values of x and y could take any suitable values that satisfy the inequality x<y. The value of y may be between 20 and 80, e.g. between 40 and 60, e.g. around 50. The value of x is preferably 1, but x could take other values. The sample(s) x may be selected from samples y according to a pattern, or randomly. For example, a sample x could be the $m^{th}$ sample in every y samples, where $1 \leq m \leq y$.

The samples may be any appropriate material to which an assaying process could be applied, e.g. soil, concrete, brick, etc.

Figure 2:
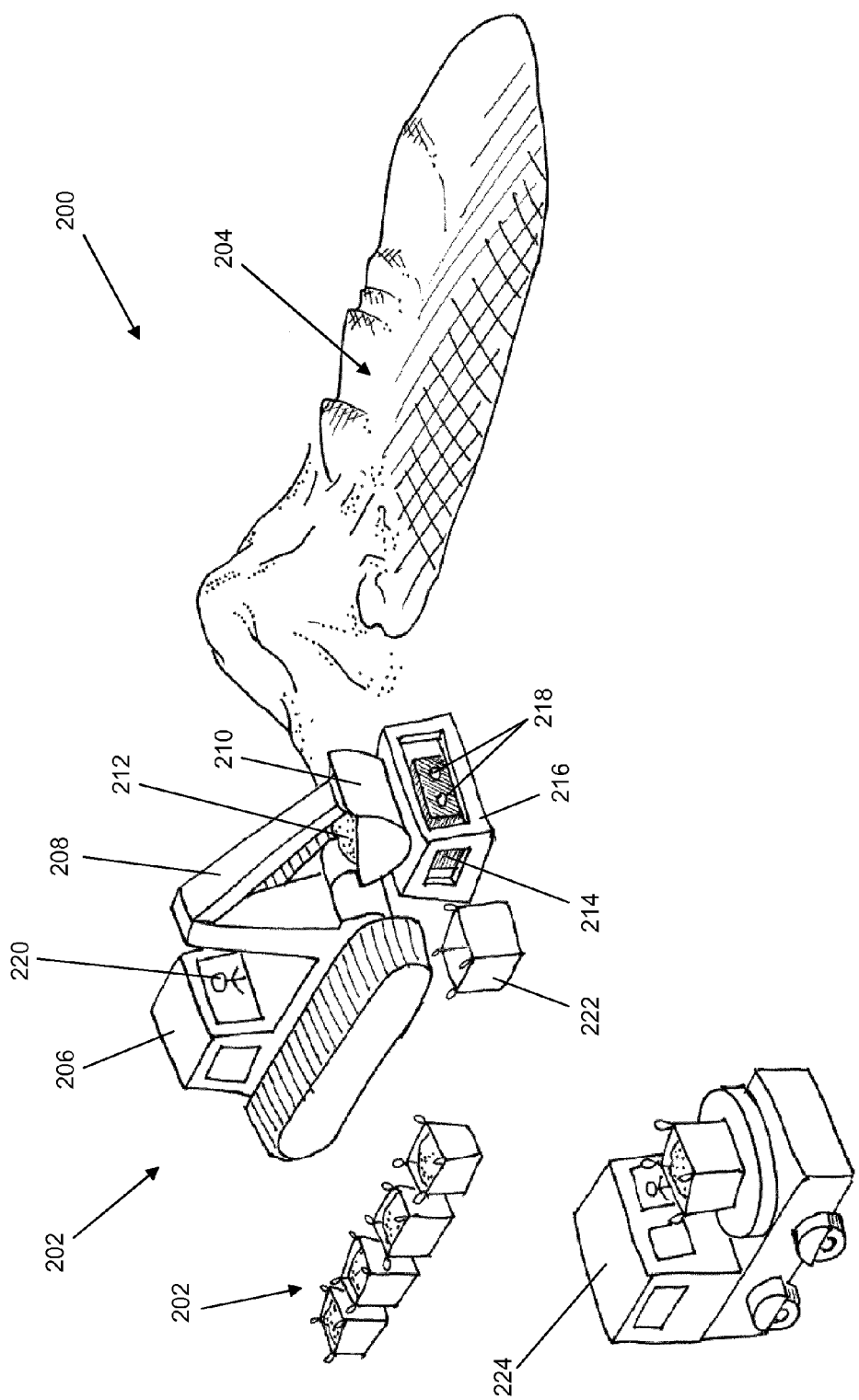

A preferred embodiment will now be described, by way of example only, with reference to the accompanying drawings in which:

FIG. 1 is a flow chart illustrating an embodiment of the method of the present invention; and FIG. 2 depicts machinery and apparatus for implementing the embodiment illustrated in FIG. 1.

FIG. 1 is a flow chart illustrating an embodiment of the method of the present invention. In this embodiment, nuclear waste material is assayed using a gross gamma detector for the activity measurement and a high resolution gamma spectrometer (HRGS) for the spectroscopic measurement. The activity derived from the gross gamma count is compared to threshold values to categorise the sample for disposal. The activity and/or threshold values are calculated based on an assumed radionuclide fingerprint for the sample.

One sample out of every 50 samples is analysed using the HRGS. The HRGS assesses the actual fingerprint of the sample. An on-site processor in communication with the HRGS processes the data obtained for the sample to determine whether it corroborates the assumed fingerprint.

If the assumed fingerprint is corroborated, this indicates that the threshold comparisons calculated from the assumed fingerprint are appropriate, and therefore that the categorisation of the material is correct. If the assumed fingerprint is not corroborated, this indicates the thresholds may not be appropriate, and that the categorisation of the waste may be incorrect. In that case, an alarm is raised to prevent any previously characterised samples from leaving the site. To continue monitoring, a new fingerprint may be obtained e.g. by performing additional tests of selected samples off-site. The new fingerprint is used to re-calibrate the gross gamma detector and calculate new threshold values, and the assaying process is recommenced. Previously tested samples may be re-tested as necessary using the gross gamma detector.

The process starts at step 100, where the gross gamma detector and the high resolution gamma spectrometer (HRGS) are initialised. This step would typically occur at the start of a project, or when a project is resumed following a break (e.g. at the start of each day of the project). The initialization step 100 comprises calibrating the gross gamma detector and setting threshold values for an assumed radionuclide fingerprint. Two threshold values are used: a lower threshold indicates that a sample should be categorised as Very Low Level Waste (VLLW) and a higher threshold indicates that a sample should be categorised as Low Level Waste (LLW), or higher.

This calibration is necessary because the gross gamma detector directly determines only the gross gamma count rather than the specific activity of a sample which is required to assess the contamination level and characterise the material for disposal. The relationship between the specific activity and the gross gamma count depends upon the radionuclide fingerprint, i.e. the radionuclide ratios in the sample. As the gross gamma detector determines only the gross gamma count and not the radionuclide fingerprint, the fingerprint must be assumed or otherwise determined and then corresponding thresholds provided to the gross gamma detector to enable the sample to be categorised. The activity thresholds specified for categorisation may be translated into corresponding gross count thresholds.

The assumed fingerprint is determined by performing high accuracy measurements, typically off-site, for selected samples. However, as an alternative, the fingerprint could be assumed based on information about the material mass and the site. For example, the fingerprint could be inferred from the history of the site, e.g. the nature of the nuclear operations that took place on the site.

The fingerprint is used, via a Monte Carlo process, to determine a relationship between gross gamma count and specific activity for that particular fingerprint. The Monte Carlo calculation also uses parameters relating to the physical arrangement of the gross gamma detector and sample material container. For example, these parameters include the size, shape, material and thickness of an excavator bucket in which the sample is held during the activity measurement. Thresholds corresponding to certain activity levels are determined from the relationship and provided to the gross gamma detector.

Following initialization and calibration, the method proceeds to step 102 which begins the count of the 50 samples from which one sample is selected for the HRGS analysis. At step 102, a counter is set to 1. The counter of the present embodiment comprises a computer program that is provided as part of a software package on a data processor that forms part of the gross gamma detector. Each time a measurement is performed, the counter automatically increments. When the counter reaches 50, the program generates a notification to alert the operator that the sample should be sent for HRGS analysis. However, in other embodiments alternative counters could be used, e.g. a computer-based counter incremented manually by the operator, or non-computer based counters such as a simple tally maintained by the operator. An automatic counter may be preferable as this may help to avoid counting errors.

As the present method is repeated for each sample, step 104 provides a check of whether there is any material left to be processed. The method may continue until all material that is designated for processing has been sampled, tested and either released or characterised for disposal. In that case, the method proceeds to step 106. If all material that is designated to be tested (e.g. for that day, or for the entire project) has been processed, the method may stop temporarily or permanently.

At step 106, the $n^{th}$ sample is selected for a gross gamma count measurement. The sample is moved to the gross gamma detector where the measurement is performed.

At step 108, it is determined whether the gross gamma count or activity exceeds the threshold values set for the gross gamma detector. If the gross gamma count exceeds the threshold corresponding to LLW, the gross gamma detector indicates this to the operator by displaying a red light. Otherwise, if the gross gamma count exceeds the threshold corresponding to VLLW, an amber light is displayed. Otherwise, a green light is displayed, indicating that the sample is "clean" and can be re-used. The thresholds may be set to correspond to any suitable specific activity value, depending on the nature of the land remediation project or other waste assaying project. In this case, conservative values are used initially, but the values are adjusted on a monthly basis, for example, the thresholds may be increased if it is determined that too many samples are being treated as VLLW when in fact they are safe to be designated "clean" and re-used.

If, at step 108, the gross gamma detector shows a green light, the method proceeds to step 110, where it is determined whether the sample count has yet reached 50. If the sample count has not yet reached 50, the method proceeds to step 112, where the sample counter is incremented by 1. The method then returns to step 104, and if appropriate thereafter to step 106, where the next sample is selected for a gross gamma count.

If, at step 110, it is determined that the counter has reached 50, the sample is transferred from the gross gamma detector to the HRGS for a high resolution analysis at step 114. The analysis determines the actual fingerprint of the sample, which includes the specific activity for each radionuclide peak. Concurrently with step 114 (and also with subsequent steps 116, 118 or 120 as applicable), the method returns to step 102, where the sample counter is reset to 1. The method then performs step 104 and 106, i.e. gross gamma count measurements of new samples, while the HRGS measurement is performed for the 50$^{th}$ sample from the previous sample set. This makes the method more efficient, as the gross gamma detector is not left inactive while the HRGS measurement is carried out.

At step 116, it is determined whether the fingerprint measured using the HRGS corroborates the assumed fingerprint. The HRGS processor includes a specific gamma library, which contains information on the specific gamma emitters that, based on the assumed fingerprint, are believed to be in the samples. The specific gamma library lists gamma emission peaks that are expected to be observed in the sample fingerprint. If all of the peaks that are expected are in fact observed, then the HRGS data is deemed to corroborate the assumed fingerprint. If any of the peaks are missing, the assumed fingerprint is not corroborated. An example fingerprint obtained using an HRGS spectroscopic measurement is shown in table 1.

TABLE 1

Fingerprint Activity Assessment

| Radionuclide | Specific activity (Bqg$^{-1}$) |
|---|---|
| H-3 | $1.22 \times 10^{-1}$ |
| C-14 | $6.06 \times 10^{-3}$ |
| Cs-137 | 1.39 |
| Sr-90 | $1.27 \times 10^{-3}$ |
| Pu-238 | $2.82 \times 10^{-3}$ |
| Pu-239 | $5.74 \times 10^{-3}$ |
| Pu-240 | $5.73 \times 10^{-3}$ |
| Pu-241 | $6.16 \times 10^{-2}$ |
| Am-241 | $1.01 \times 10^{-2}$ |
| Total | 1.73 |

If the assumed fingerprint is corroborated, this indicates that the thresholds are appropriate, and that the gross gamma detector has correctly categorised the sample as having a specific activity that is below the VLLW contamination threshold. The method then proceeds to step 118, where the sample is designated "clean" and suitable to be released for re-use. As discussed above, the method started steps 102, 104 and 106 for new samples, which were commenced at step 114 and performed concurrently with steps 114-120. Following step 118, the method continues with the gross gamma count measurements that have already been started at steps 102-106.

The data obtained in the HRGS measurement is transmitted in real time to an off-site computer. Before the end of each day, prior to removal of any samples from the site, the data is reviewed by a specialist operator to verify the assumed fingerprint. The specialist examines the measured fingerprints e.g. to determine whether there are any additional peaks that are not present in the assumed fingerprint. This additional check performed by a human operator can identify deficiencies in the assumed fingerprint that may not be identified by the automatic check, e.g. while the automatic check may identify missing peaks that are expected in the fingerprint, the human check may identify additional peaks that are not consistent with the assumed fingerprint. This provides the benefit of an additional level of confidence that the material categorisation based on the gross gamma count measurement can be relied on. If there are additional peaks, then the samples can be prevented from leaving the site. Consequently a new fingerprint may be obtained e.g. through further testing. The assaying process may be resumed using the new fingerprint. Samples from the previous assaying may be re-tested.

If the assumed fingerprint is not corroborated, the method proceeds to step 120. At step 120, the assaying process is halted. Further testing of selected samples may be carried out at an off-site laboratory to obtain a new fingerprint. The new fingerprint is used to calculate new threshold values for the gross gamma detector.

As the assumed fingerprint was determined to be inappropriate, this means that the gross gamma count measurements performed since the fingerprint was last corroborated by an HRGS measurement may not be reliable. The last 50 samples are therefore designated for re-testing. As discussed above, the method had already started steps 102, 104 and 106 for new samples, which were commenced at step 114 and performed concurrently with steps 114-120. These new samples are also designated for re-testing. The method may recommence, using a fingerprint, at step 102, proceeding to steps 104 and 106 with a reselection of one of the 50 samples for activity measurement.

If it is determined at step 108 that the gross gamma count of a sample indicates that the specific activity is above the VLLW or the LLW contamination threshold, the sample is transferred to the HRGS which, at step 122, determines the specific activity and radionuclide fingerprint of the sample, and characterises the sample for appropriate disposal.

Then, at step 124, it is determined whether the sample count has yet reached 50. If the sample count has reached 50 the method reverts to step 102, which resets the counter to 1, and then proceeds to step 104. As the sample is the 50th sample, an additional step (not shown) may be included, in which an automatic check is performed to determine whether the fingerprint corroborates the assumed fingerprint and, if necessary, the assaying is halted. If the count has not yet reached 50, the method increments the counter at step 126, and then reverts back to step 104, maintaining the sample count.

FIG. 2 shows a site 200 designated for land remediation, e.g. following decommission of a nearby nuclear energy generation plant. On the site 200 is a collection of machinery and apparatus 202 carrying out the material assaying method of the present invention.

An area 204 of the land designated for remediation has been excavated in order to obtain samples for testing, characterisation, and subsequently release for reuse or disposal as appropriate. Excavator 206 having an arm digger 208 comprising a bucket 210 has excavated land area 204. The excavator 206 has removed a sample 212 from the excavated area 204 to be tested with a gross gamma detector 214. Once the sample 212 has been collected in the bucket 210, it is placed over the top of the gross gamma detector 214. The gross gamma detector 214 is provided with a robust housing 216 to ensure that the bucket 210 does not cause damage to the gross gamma detector 214 when the excavator 206 lowers it towards the gross gamma detector 214.

After about 10 seconds, the gross gamma detector 214 indicates via means of coloured lights 218 whether the sample 212 has a specific activity that exceeds a LLW or VLLW contamination threshold. (Equivalent coloured lights are also provided on the side of the gross gamma detector 214 that is visible to the operator 220 of the excavator 206.) The gross gamma detector 214 maintains a count of the number of samples that it has tested.

As described with reference to FIG. 1 above, the specific activity is inferred from an assumed fingerprint and parameters relating to the bucket 210, based on a Monte Carlo simulation.

If the gross gamma detector 214 determines that the sample exceeds a VLLW contamination threshold, the sample 212 is deposited in a bag 222. The bag 222 has dimensions of 1 m$^3$. The bag 222 is then transferred without delay to a high resolution gamma spectrometer (HRGS) 224 for a high resolution gamma spectroscopy measurement. The HRGS 224 is used to characterise the sample 212 to determine its specific activity and radionuclide fingerprint, and to designate it for disposal according to its characterisation.

If the sample 212 is determined by the gross gamma detector 214 to have a specific activity that is below the VLLW contamination threshold, and if the sample count has not yet reached 50, the sample 212 is placed in the bag 222 and moved to a temporary storage area 226 for samples determined by the gross gamma detector 214 to be uncontaminated. The counter is incremented and a new sample selected.

However, if the sample 212 is the 50th sample, it is placed in the bag 222 and transferred to the HRGS 224 for a high resolution gamma spectroscopy analysis. For the example of a 1 m$^3$ bag, the analysis typically takes about 5-15 minutes. The HRGS 224 assesses the fingerprint of the sample. The HRGS automatically determines whether the measured fingerprint corroborates the assumed fingerprint from which the VLLW and LLW threshold where calculated.

If the assumed fingerprint is corroborated, this indicates that the thresholds for the gross gamma detector 214 are appropriate, and the sample 212 is therefore below a VLLW contamination threshold as previous determined. If that is the case, the sample 212, and the preceding samples stored in sample area 226 that were determined to be below a contamination threshold, are designated for release and reuse as being "clean".

If the assumed fingerprint is not corroborated, this indicates that the previous 50 sample measurements conducted by the gross gamma detector 214 may be unreliable. The assaying process is therefore temporarily halted, and the fingerprint may be assessed in more detail e.g. off site. If necessary, a new fingerprint may be obtained by testing samples at an off-site laboratory. The new fingerprint is used to set new thresholds for the gross gamma detector 214. Sample 212, and the samples that the gross gamma detector 214 unreliably deemed to be uncontaminated, are returned to the gross gamma detector 214 for retesting with the new fingerprint.

This method is then continued, with further areas of the site 200 being excavated and samples selected therefrom. Every 50$^{th}$ sample is sent to an additional test at the HRGS apparatus 224, the results of which inform the disposal, release, or retesting of the sample.

It will be appreciated by those skilled in the art that only one possible embodiment has been described and that many variations and modifications are possible within the scope of the invention. For example, samples could be selected for high resolution testing more or less frequently than 1 in every 50. The continued excavation of the site, and a selection of a further 50 samples, might be delayed until the high resolution measurement of the selected sample has been completed. However, it is preferable for the testing of the next 50 samples to be commenced while the previous selected 50$^{th}$ sample is being tested by the HRGS, in anticipation of the fingerprint being corroborated. Such concurrent measurements would save time as the next 50 samples would only need to be restarted, thus losing time, if the fingerprint were found to be inappropriate.

The invention claimed is:

1. A method of assaying potentially radioactive material comprising:
   selecting a plurality of samples from a material mass on a site;
   performing, on the site, an activity measurement based on a gross count of each sample of the plurality of samples, and comparing the activity measurement with at least one activity threshold in order to categorize radioactivity of each sample for disposal purposes, wherein at least one of the activity measurement or the at least one threshold is based on an assumed parameter set;
   selecting a sample x from every y samples of the plurality of samples, where x<y;
   performing, on the same site, a spectroscopic measurement of emitted radiation from the sample x; and
   automatically determining whether the spectroscopic measurement corroborates the assumed parameter set before the y samples leave the site for disposal purposes.

2. The method of claim 1, wherein the activity measurement and the spectroscopic measurement are performed concurrently.

3. The method of claim 1, wherein the automatically determining whether the spectroscopic measurement corroborates the assumed parameter set is carried out immediately after performing the spectroscopic measurement.

4. The method of claim 1, further comprising: a non-automatic step carried out by a human to determine whether the spectroscopic measurement for the sample x verifies the assumed parameter set.

5. The method of claim 4, wherein the non-automatic step is carried out off-site.

6. The method of claim 4, further comprising: preventing the y samples from leaving the site when the non-automatic step for the sample x does not verify the assumed parameter set.

7. The method of claim 4, further comprising obtaining a new parameter set when the non-automatic step for the sample x does not verify the assumed parameter set.

8. The method of claim 7, comprising: continuing the activity measurement for the plurality of samples using at least one new threshold based on the new parameter set.

9. The method of claim 4, wherein the non-automatic step is carried out at least once per day.

10. The method of claim 1, wherein spectroscopic data obtained in the spectroscopic measurement is transmitted off-site for review on a same day as the performing of the spectroscopic measurement.

11. The method of claim 1, wherein categorizing comprises determining whether each sample is safe to leave the site.

12. The method of claim 1, further comprising: preventing the y samples from leaving the site when the spectroscopic measurement for the sample x does not corroborate the assumed parameter set.

13. The method of claim 1, further comprising: obtaining a new parameter set when the spectroscopic measurement for the sample x does not corroborate the assumed parameter set.

14. The method of claim 1, wherein the activity measurement is based on a gross gamma count.

15. The method of claim 1, wherein the activity measurement is completed within a period of less than 30 seconds for each sample.

16. The method of claim 1, wherein the spectroscopic measurement comprises a high resolution gamma spectroscopy (HGRS) analysis.

17. The method of claim 1 wherein the spectroscopic measurement is completed within a period of no greater than 15 minutes for each sample.

18. The method of claim 1, wherein the assumed parameter set comprises a radionuclide fingerprint.

19. The method of claim 18, wherein the automatically determining whether the spectroscopic measurement corroborates the assumed parameter set comprises: determining whether at least one expected peak associated with at least one radionuclide included in the radionuclide fingerprint is present in the spectroscopic measurement, wherein the radionuclide fingerprint is corroborated if the at least one expected peak is present in the spectroscopic measurement.

20. The method of claim 18, further comprising a non-automatic step carried out by a human to verify the radionuclide fingerprint, the non-automatic step comprising: determining whether any peaks are present in the spectroscopic measurement that are not associated with at least one radionuclide included in the radionuclide fingerprint, wherein the radionuclide fingerprint is verified if no peaks are present in the spectroscopic measurement that are not included in the radionuclide fingerprint.

* * * * *